United States Patent
Davis et al.

(10) Patent No.: US 10,682,059 B1
(45) Date of Patent: Jun. 16, 2020

(54) RADIO FREQUENCY APPLICATOR AND THERMOACOUSTIC IMAGING SYSTEM EMPLOYING THE SAME

(71) Applicant: ENDRA Life Sciences Inc., Ann Arbor, MI (US)

(72) Inventors: Christopher Nelson Davis, Ann Arbor, MI (US); Charlton Chen, Northville, MI (US); Michael M. Thornton, London (CA)

(73) Assignee: ENDRA Life Sciences Inc., Ann Arbor, MI (US)

( * ) Notice: Subject to any disclaimer, the term of this patent is extended or adjusted under 35 U.S.C. 154(b) by 0 days.

(21) Appl. No.: 16/235,039

(22) Filed: Dec. 28, 2018

(51) Int. Cl.
*A61B 5/00* (2006.01)
*G01N 29/24* (2006.01)
*A61B 8/00* (2006.01)

(52) U.S. Cl.
CPC .......... *A61B 5/0093* (2013.01); *A61B 8/4416* (2013.01); *G01N 29/2431* (2013.01); *A61B 2562/12* (2013.01)

(58) Field of Classification Search
None
See application file for complete search history.

(56) References Cited

U.S. PATENT DOCUMENTS

| | | | |
|---|---|---|---|
| 7,609,504 B2 | 10/2009 | Park et al. | |
| 8,178,457 B2 | 5/2012 | de Rochemont | |
| 8,593,819 B2 | 11/2013 | de Rochemont | |
| 9,520,649 B2 | 12/2016 | de Rochemont | |
| 9,927,484 B2 | 3/2018 | Kwon et al. | |
| 9,979,062 B2 | 5/2018 | Deriso | |
| 10,139,215 B2 | 11/2018 | Folgero et al. | |
| 2002/0109558 A1* | 8/2002 | Kanamaluru | H01P 1/161 333/21 A |
| 2006/0003152 A1* | 1/2006 | Youngs | H01B 1/22 428/212 |
| 2012/0093041 A1* | 4/2012 | Takeda | H04B 1/034 370/280 |
| 2013/0079599 A1* | 3/2013 | Holmes | G06F 19/3418 600/300 |
| 2017/0023635 A1 | 1/2017 | Kwon et al. | |

* cited by examiner

*Primary Examiner* — Joel F Brutus
(74) *Attorney, Agent, or Firm* — Stanley E. Jelic

(57) ABSTRACT

A radio frequency applicator comprises an open-ended, hollow waveguide having an aperture therein. A solid insert is positioned within the waveguide. The solid insert has a recess formed therein that is aligned with the aperture. Filler material is provided between facing surfaces of the waveguide and the insert to fill gaps therebetween. A radio frequency (RF) source extends through the aperture and into the recess and is configured to generate RF energy pulses.

12 Claims, 3 Drawing Sheets

RADIO FREQUENCY APPLICATOR AND THERMOACOUSTIC IMAGING SYSTEM EMPLOYING THE SAME

FIELD

The subject disclosure relates to thermoacoustic imaging and in particular, to a radio frequency (RF) applicator and a thermoacoustic imaging system employing the same and to a method of assembling a radio frequency applicator.

BACKGROUND

In high frequency systems, it is common to employ waveguides to guide electromagnetic waves or sound with minimal loss of energy by restricting expansion of the electromagnetic waves propagating within the waveguides to one or two dimensions. Depending on the nature of the electromagnetic waves to be propagated, the waveguides may take different forms. Also, in many instances, filters are employed to allow electromagnetic waves at some frequencies to pass and travel along the waveguides, while rejecting electromagnetic waves at other frequencies. For example, when propagating radio frequency (RF) waves, hollow, open-ended, conductive metal waveguides are often employed. In some instances to provide the desired filtering, these hollow metal waveguides are fitted with a solid insert formed of high dielectric constant material.

Waveguides such as those described above have been employed in thermoacoustic imaging systems. Thermoacoustic imaging is an imaging modality that provides information relating to the thermoelastic properties of tissue. Thermoacoustic imaging uses short pulses of electromagnetic energy, such as RF pulses, directed into a subject to heat absorbing features within the subject rapidly, which in turn induces acoustic pressure waves that are detected using acoustic receivers such as one or more thermoacoustic or ultrasound transducer arrays. The detected acoustic pressure waves are analyzed through signal processing, and processed for presentation as thermoacoustic images that can be interpreted by an operator.

In order to direct RF pulses into the subject during thermoacoustic imaging, a radio frequency (RF) applicator employing a waveguide is coupled to tissue adjacent a region of interest (ROI) within the subject to be imaged. Sub-optimal coupling of the RF applicator to the tissue may cause issues such as inefficient energy transfer, reduced heating rates, reduced signal intensity, non-uniform energy deposition, tissue hotspots, tissue overheating, RF power supply damage, and poor image quality. Factors that lead to sub-optimal coupling of the RF applicator to the tissue include variability in the size of the subject, the size of tissue within the subject, the geometry of tissue within the subject, the composition of tissue within the subject, etc.

During fabrication of waveguides fitted with solid inserts, air gaps can form between the facing surfaces of the waveguides and the solid inserts. Unfortunately, the air gaps can change the frequency characteristics of the waveguides in an unpredictable manner. As will be appreciated, improvements are therefore desired. It is therefore an object at least to provide a novel radio frequency (RF) applicator and a thermoacoustic imaging system employing the same and a novel method of assembling a radio frequency applicator.

SUMMARY

It should be appreciated that this Summary is provided to introduce a selection of concepts in a simplified form that are further described below in the Detailed Description. This Summary is not intended to be used to limit the scope of the claimed subject matter.

Accordingly, in one aspect there is provided a radio frequency applicator comprising: an open-ended, hollow waveguide having an aperture therein; a solid insert within the waveguide, the solid insert having a recess formed therein that is aligned with said aperture; filler material between facing surfaces of the waveguide and the insert to fill gaps therebetween; and a radio frequency (RF) source extending through the aperture and into the recess and being configured to generate RF energy pulses.

In one or more embodiments, the insert is formed of ceramic material. The ceramic material may have a real relative permittivity greater than 10, such as between about 57 and 63, and a loss tangent less than 0.01.

In one or more embodiments, the filler material has a melting point in the range of from about 40 and 120 degrees Centigrade. The filler material may be in the form of a ceramic wax composite. The ceramic wax composite may have a real relative permittivity between about 30 and 50 and an imaginary relative permittivity between about 2 and 7. For example, the ceramic wax composite may comprise 69% to 80% by weight titanium dioxide, 10% to 15% by weight wax and 4% to 13% by weight graphite.

In one or more embodiments, the filler material is one of: (i) a ceramic wax composite; (ii) a conductive paste; (iii) a conductive grease; and (iv) a ceramic powder and gel wax mixture.

According to another aspect there is provided a system for enhancing radio frequency energy delivery to a tissue region of interest comprising an object of interest and a reference that are separated by at least one boundary, the system comprising: a thermoacoustic imaging system comprising a radio frequency (RF) applicator according to any one of paragraphs [0007] to [0009] configured to emit RF energy pulses into the tissue region of interest and heat tissue therein and an acoustic receiver configured to receive acoustic signals generated in response to heating of tissue in the tissue region of interest; and one or more processors configured to: process received acoustic signals and generate a thermoacoustic image of the tissue region of interest.

According to another aspect there is provided a method of assembling a radio frequency (RF) applicator comprising: covering a ceramic insert with a coating, wherein the ceramic insert has dimensions that substantially match an internal volume of an open-ended, hollow waveguide, and wherein the ceramic insert has a recess therein configured to accept a radio frequency emitter; heating the waveguide to a temperature that is above a melting point of the coating; placing the coated ceramic insert into the internal volume of the heated waveguide, wherein the internal volume is completely filled except for the recess; and cooling the waveguide, ceramic insert, and coating to a temperature below the melting point of the coating so that the coating solidifies and fills gaps between the facing surfaces of the insert and the waveguide.

In one or more embodiments, the waveguide has an aperture therein that is aligned with the recess when the coated ceramic insert is placed into the internal volume of the heated waveguide. The method further comprises inserting a radio frequency emitter through the aperture and into the recess.

In one or more embodiments, the method further comprises, prior to the step of applying the coating to the ceramic insert, removing entrained air bubbles in the coating. The removing may be performed by heating and cooling the coating in one or more cycles.

In one or more embodiments, the method further comprises adjusting the radio frequency emitter so that the frequency of RF pulses emitted by the RF applicator match a desired frequency. The adjusting may comprise one of adjusting the extent to which the radio frequency emitter extends into the recess, and inserting dielectric material between the radio frequency emitter and the ceramic insert.

BRIEF DESCRIPTION OF THE DRAWINGS

Embodiments will now be described more fully with reference to the accompanying drawings in which.

DETAILED DESCRIPTION OF EMBODIMENTS

Figure 1:
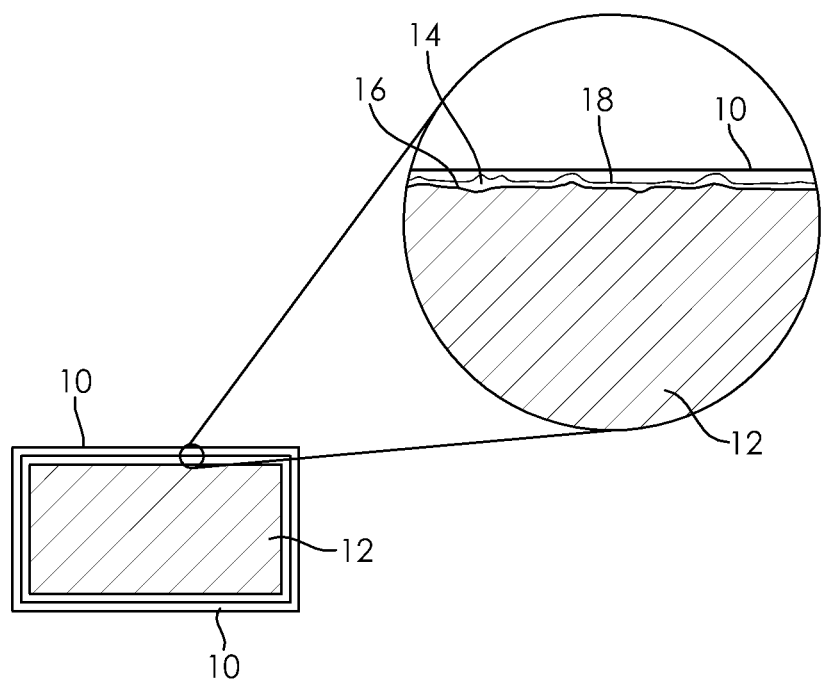
FIG. 1 is a schematic view of a high dielectric constant insert positioned between a pair of electrodes showing imperfections in a surface of the high dielectric constant insert.

The foregoing summary, as well as the following detailed description of certain examples will be better understood when read in conjunction with the appended drawings. As used herein, an element or feature introduced in the singular and preceded by the word "a" or "an" should be understood as not necessarily excluding the plural of the elements or features. Further, references to "one example" or "one embodiment" are not intended to be interpreted as excluding the existence of additional examples or embodiments that also incorporate the described elements or features. Moreover, unless explicitly stated to the contrary, examples or embodiments "comprising" or "having" or "including" an element or feature or a plurality of elements or features having a particular property may include additional elements or features not having that property. Also, it will be appreciated that the terms "comprises", "has", "includes" means "including but not limited to" and the terms "comprising", "having" and "including" have equivalent meanings.

As used herein, the term "and/or" can include any and all combinations of one or more of the associated listed elements or features.

It will be understood that when an element or feature is referred to as being "on", "attached" to, "connected" to, "coupled" with, "contacting", etc. another element or feature, that element or feature can be directly on, attached to, connected to, coupled with or contacting the other element or feature or intervening elements may also be present. In contrast, when an element or feature is referred to as being, for example, "directly on", "directly attached" to, "directly connected" to, "directly coupled" with or "directly contacting" another element of feature, there are no intervening elements or features present.

It will be understood that spatially relative terms, such as "under", "below", "lower", "over", "above", "upper", "front", "back" and the like, may be used herein for ease of description to describe the relationship of an element or feature to another element or feature as illustrated in the figures. The spatially relative terms can however, encompass different orientations in use or operation in addition to the orientations depicted in the figures.

Reference herein to "example" means that one or more feature, structure, element, component, characteristic and/or operational step described in connection with the example is included in at least one embodiment and/or implementation of the subject matter according to the subject disclosure. Thus, the phrases "an example," "another example," and similar language throughout the subject disclosure may, but do not necessarily, refer to the same example. Further, the subject matter characterizing any one example may, but does not necessarily, include the subject matter characterizing any other example.

Reference herein to "configured" denotes an actual state of configuration that fundamentally ties the element or feature to the physical characteristics of the element or feature preceding the phrase "configured to".

Unless otherwise indicated, the terms "first," "second," etc. are used herein merely as labels, and are not intended to impose ordinal, positional, or hierarchical requirements on the items to which these terms refer. Moreover, reference to a "second" item does not require or preclude the existence of a lower-numbered item (e.g., a "first" item) and/or a higher-numbered item (e.g., a "third" item).

As used herein, the terms "approximately" and "about" represent an amount close to the stated amount that still performs the desired function or achieves the desired result. For example, the terms "approximately" and "about" may refer to an amount that is within engineering tolerances that would be readily appreciated by a person of ordinary skill in the art.

In the following, a radio frequency (RF) applicator and a thermoacoustic imaging system employing the same are described. Generally, the radio frequency applicator comprises an open-ended, hollow waveguide having an aperture therein. A solid insert is positioned within the waveguide. The solid insert has a recess formed therein that is aligned with the aperture. Filler material is provided between facing surfaces of the waveguide and the insert to fill gaps therebetween. A radio frequency (RF) source extends through the aperture and into the recess and is configured to generate RF energy pulses.

As mentioned previously, if air gaps between the solid insert and the waveguide exist, the overall permittivity inside the waveguide may deviate from the desired permittivity resulting in a change in the frequency that RF pulses are efficiently emitted by the RF applicator. For example, FIG. 1 shows a pair of electrodes 10 and a high dielectric constant insert 12 positioned between the electrodes 10. Imperfections in facing surfaces of the electrodes 10 and high dielectric constant insert 12 result in air gaps between the electrodes and the high dielectric constant insert. The air gaps act as a capacitor, which can change the desired electrical characteristics of the electrode pair and high dielectric constant insert arrangement. The inset in FIG. 1 shows for example, at a microscopic level, imperfections 14 in a surface 16 of the high dielectric constant insert 12 resulting in air gaps 18 between the high dielectric constant insert 12 and the electrode 10 abutting surface 16.

One technique to eliminate air gaps between the electrodes 10 and the high dielectric constant insert 12 is to directly apply the electrodes 10 onto the high dielectric constant insert 12 in such a way that avoids formation of air gaps. For example, the electrodes 10 may take the form of an epoxy loaded with silver or other conductive material therein that can be deposited onto the surfaces of the high dielectric constant insert 12 via sputtering. Conductive epoxies unfortunately have the disadvantage that they contain non-conductive binder material. When a conductive epoxy is employed and is applied to the high dielectric constant insert 12, at locations where non-conductive binder material makes direct contact with the high dielectric constant insert 12 rather than the conductive material within the epoxy, the non-conductive binder material electrically behaves in the same manner as air gaps. If the epoxy is heated to remove the non-conductive binder material after application, voids between the electrodes 10 and the high dielectric constant insert 12 form resulting in air gaps between the electrodes and the high dielectric constant insert. As a result, conductive epoxies of this nature are not ideal.

Figure 2:
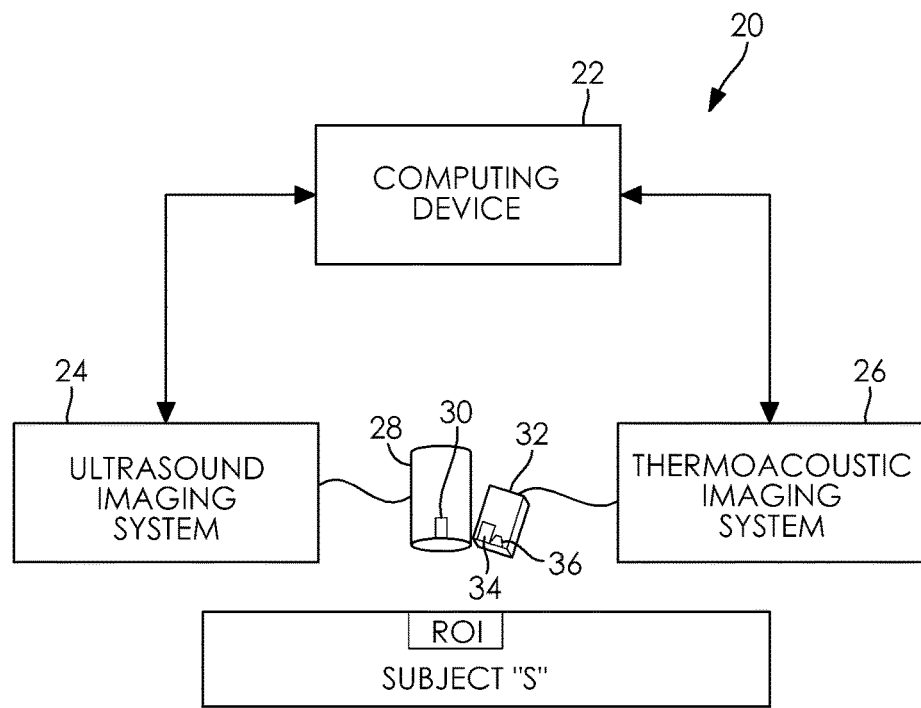
FIG. 2 is a schematic view of an imaging system.
Figure 3:
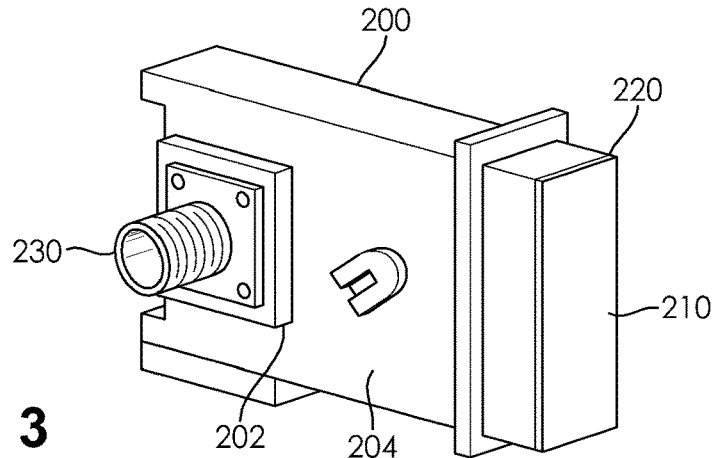
FIG. 3 is a perspective view of a radio frequency (RF) applicator forming part of the imaging system of FIG. 2.
Figure 4:
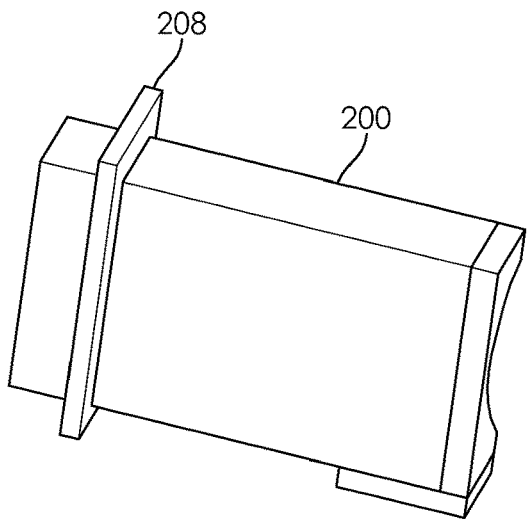
FIG. 4 is another perspective view of the RF applicator of FIG. 3.
Figure 5:
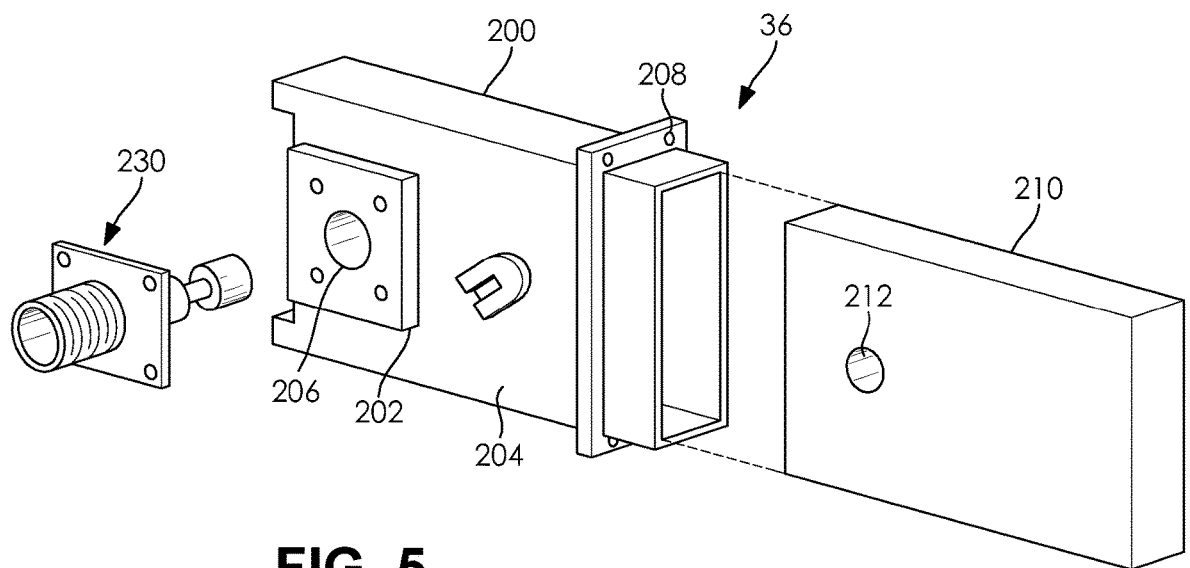
FIG. 5 is an exploded perspective view of the RF applicator of FIG. 3.
Figure 6:
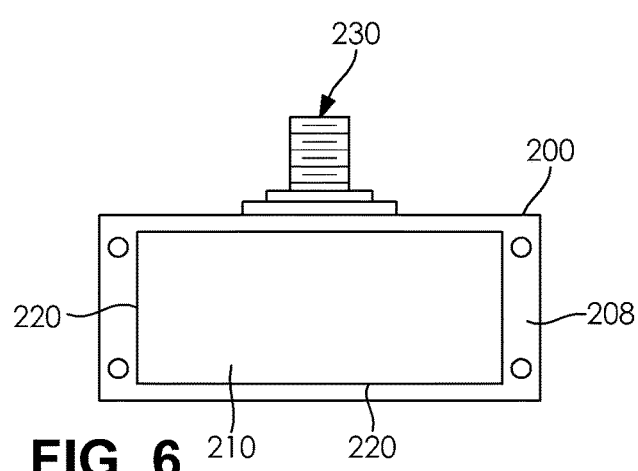
FIG. 6 is an end view of the RF applicator of FIG. 3.
Figure 7:
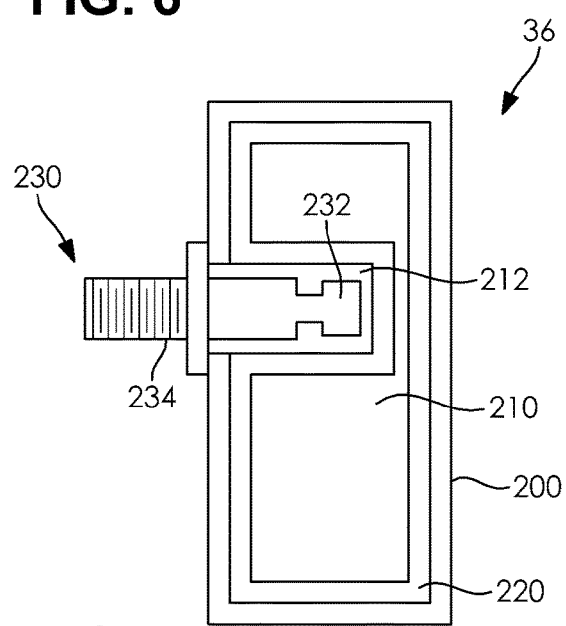
FIG. 7 is a cross-sectional view of the RF applicator of FIG. 3.

Turning now to FIG. 2, an exemplary imaging system is shown and is generally identified by reference numeral 20. As can be seen, the imaging system 20 comprises a programmed computing device 22 communicatively coupled to an ultrasound imaging system 24 and to a thermoacoustic imaging system 26. The ultrasound imaging system 24 and thermoacoustic imaging system 26 are configured to obtain ultrasound image data and thermoacoustic image data, respectively, of a tissue region of interest ROI associated with a subject S.

The programmed computing device 22 in this embodiment is a personal computer or other suitable processing device comprising, for example, a processing unit comprising one or more processors, system memory (volatile and/or non-volatile memory), other non-removable or removable memory (e.g., a hard disk drive, RAM, ROM, EEPROM, CD-ROM, DVD, flash memory, etc.) and a system bus coupling the various computer components to the processing unit. The computing device 22 may also comprise networking capabilities using Ethernet, Wi-Fi, and/or other suitable network format, to enable connection to shared or remote drives, one or more networked computers, or other networked devices. One or more input devices, such as a mouse and a keyboard (not shown) are coupled to the computing device 22 for receiving operator input. A display device (not shown), such as one or more computer screens or monitors, is coupled to the computing device 22 for displaying one or more generated images that are based on ultrasound image data received from the ultrasound imaging system 24 and/or the thermoacoustic image data received from thermoacoustic imaging system 26.

The ultrasound imaging system 24 comprises an acoustic receiver in the form of an ultrasound transducer 28 that houses one or more ultrasound transducer arrays 30 configured to emit sound waves into the region of interest ROI of the subject S. The sound waves directed into the region of interest ROI of the subject echo off tissue within the region of interest ROI, with different tissues reflecting varying degrees of sound. Echoes that are received by the one or more ultrasound transducer arrays 30 are processed by the ultrasound imaging system 24 before being communicated as ultrasound image data to the computing device 22 for further processing and for presentation as ultrasound images that can be interpreted by an operator. In this embodiment, the ultrasound imaging system 24 utilizes B-mode ultrasound imaging techniques assuming a nominal speed of sound of 1,540 m/s. As ultrasound imaging systems are known in the art, further specifics of the ultrasound imaging system 24 will not be described further herein.

The thermoacoustic imaging system 26 comprises an acoustic receiver in the form of a thermoacoustic transducer 32. The thermoacoustic transducer 32 houses one or more thermoacoustic transducer arrays 34 as well as a radio frequency (RF) applicator 36. It will however be appreciated that the RF applicator 36 may be housed separately from the thermoacoustic transducer 32. The RF applicator 36 is configured to emit short pulses of RF energy that are directed into tissue within the region of interest ROI of the subject. In this embodiment, the RF applicator 36 has a frequency between about 10 Mhz and 100 GHz and has a pulse duration between about 0.1 nanoseconds and 5000 nanoseconds, and more particularly between about 50 nanoseconds to 5000 nanoseconds. The RF energy pulses delivered to the tissue within the region of interest ROI heat the tissue thereby to induce acoustic pressure waves that are detected by the thermoacoustic transducer 32. The acoustic pressure waves that are detected by the thermoacoustic transducer 32 are processed and communicated as thermoacoustic image data to the computing device 22 for further processing and for presentation as thermoacoustic images that can be interpreted by the operator.

In this embodiment, the ultrasound transducer 28 and thermoacoustic transducer 32 are mechanically interconnected so that the spatial relationship between the one or more ultrasound transducer arrays 30, the one or more thermoacoustic arrays 34 and the RF applicator 36 are known. The spatial relationship is set using a centerline of the one or more ultrasound transducer arrays 34, the one or more thermoacoustic transducer arrays 34, and RF applicator 36. Each centerline is defined as being a mid-point of an area of the respective transducer array.

In this embodiment, the spatial relationship between the one or more ultrasound transducer arrays 30 and the one or more thermoacoustic transducer arrays 34 is such that the centerline of the one or more thermoacoustic transducer arrays 34 is set at a known angle α with respect to the centerline (also known as the axial axis or ultrasound transducer array beam axis) of the one or more ultrasound transducer arrays 30. The spatial relationship between the one or more thermoacoustic transducer arrays 34 and the RF applicator 36 is such that the centerline of the RF applicator 36 is spaced-apart and generally parallel to the centerline of the one or more thermoacoustic transducer arrays 34.

The imaging system 20 utilizes the known spatial relationship between the one or more ultrasound transducer arrays 30 and the one or more thermoacoustic transducer arrays 34 to increase the precision and accuracy of thermoacoustic imaging.

The coordinate system of the one or more ultrasound transducer arrays 30 of the ultrasound transducer 28 and the coordinate system of the one or more thermoacoustic transducer arrays 34 of the thermoacoustic transducer 32 are mapped by the computing device 22 so that acquired ultrasound and thermoacoustic images can be registered. Alternatively, the thermoacoustic imaging system 26 may make use of the one or more ultrasound transducer arrays 30 of the ultrasound transducer 28 by disconnecting the one or more ultrasound transducer arrays 30 from the ultrasound transducer 28 and connecting the one or more ultrasound transducer arrays 30 to the thermoacoustic transducer 32. As will be appreciated, by doing this coordinate mapping between the one or more ultrasound transducer arrays 28 and the one or more thermoacoustic transducer arrays 34 is not required.

Turning now to FIGS. 3 to 7, the RF applicator 36 is better illustrated. As can be seen, the RF applicator 36 comprises a hollow, generally rectangular, open-ended waveguide 200 formed of electrically conductive metal material. A plinth 202 is provided on surface 204 of the waveguide 200 adjacent one end thereof. A central aperture 206 is provided in the plinth 202 and extends through surface 204 of the waveguide 200. A flange 208 extends about the waveguide 200 adjacent the other end thereof.

A solid, low loss, high dielectric constant insert 210 formed of ceramic or other suitable material is positioned within the interior of the waveguide 200 and fills the internal volume of the waveguide 200. A recess 212 (see FIG. 7) is provided in the high dielectric constant insert 210 that is aligned with the aperture 206. In this embodiment, high dielectric constant refers to a real relative permittivity greater than 10 and low loss refers to a loss tangent less than 0.01.

A ceramic composite coating 220 is provided between the facing surfaces of the high dielectric constant insert 210 and the waveguide 200. The ceramic composite coating 220 fills air gaps that would otherwise form between the facing surfaces of the high dielectric constant insert 210 and the waveguide as a result of imperfections in the facing surfaces. The ceramic composite coating 220 has a dielectric constant that is similar to that of the high dielectric constant insert 210. In this manner, the ceramic composite coating 220 has little effect on the electrical characteristics of the RF applicator 36.

An RF source 230 having an RF emitter 232 at one end that is configured to generate RF energy pulses, extends through the aperture 206 and into the recess 212 so that the RF emitter 232 is suspended within the recess 212. The RF source 230 further comprises a threaded connector 234 to which control electronics are connected and a mounting flange 236 that overlies the plinth 202 and through which threaded fasteners pass and engage the plinth 202 thereby to secure the RF source 230 to the waveguide 200.

In this embodiment, the ceramic composite coating 220 is in the form of a high permittivity, ceramic wax composite comprising for example, ceramic powder together with a wax matrix material (e.g. soy wax, paraffin wax, carnauba wax, etc.). As a result, the ceramic composite coating 220 is thermally reversible, permittivity tunable, readily removable from the insert 212 or waveguide internal volume, and it is possible to work with during processing.

In this embodiment, the ceramic composite coating 200 comprises 69% to 80% titanium dioxide (rutile form), 10% to 15% wax and 4% to 13% graphite. The above percentages are by weight of the ceramic composite coating. The ceramic composite coating 220 has a thickness between about 0.5 and 50 micrometers. The ceramic composite coating 220 has a melting point between about 40 and 120 degrees Celsius. The ceramic composite coating 220 has a real relative permittivity between about 30 and 50 and an imaginary relative permittivity between about 2 and 7.

Although ceramic polymers have been widely studied, a ceramic composite coating is employed for a number of reasons. Typically, a ceramic polymer is formed by mixing a ceramic powder with an elastomer base and a curing agent. The mixture is then allowed to degas and harden. In mixtures where the ceramic powder exceeds 50% by weight of the mixture, these mixtures are highly viscous and difficult to degas. This can result in air bubbles being trapped in the final ceramic polymer. Furthermore, once hardened the ceramic polymer cannot be remolded and can be difficult to machine. The state of the ceramic composite coating 220 is however, thermally reversable (i.e. the ceramic composite coating can be remolded by raising the temperature above its melting point). Also, the ceramic composite coating 220 is less likely to have air bubbles trapped therein as it can be degassed at atmospheric pressure by heating the ceramic composite coating (varying for a period of time from about 10 minutes to 2 hours). Also, this degassing step can be repeated, which is not possible with a typical ceramic polymer as typical ceramic polymers cannot be degassed once hardened.

During assembly of the RF applicator 36, the ceramic composite coating 220 is applied to the external surfaces of the high dielectric constant insert 210 that will face the interior surfaces of the waveguide 200 when the insert has been positioned within the internal volume of the waveguide. The waveguide 200 is then heated to a temperature that is above a melting point of the ceramic composite coating 220 and the insert 210 is positioned within the waveguide 200 to fill its internal volume and so that the recess 212 is aligned with the aperture 206. During this process, the ceramic composite coating 220 melts as a result of the heated waveguide 200 allowing the ceramic composite coating to flow and fill gaps between the facing surfaces of the insert 210 and the waveguide 200 resulting from surface imperfections. Thereafter, the waveguide 200, insert 210, and ceramic composite coating 220 are cooled to a temperature below the melting point of the ceramic composite coating so that the ceramic composite coating solidifies. A check is then made to see if any ceramic composite coating 220 has flowed into the recess 212 and if so, any ceramic composite coating in the recess 212 is removed. At this stage, the RF source 230 can be installed on the waveguide 200 by affixing the mounting flange 236 to the plinth 202 and with the RF emitter 232 positioned in the recess 212.

If desired, prior to the step of applying the ceramic composite coating 220 to the insert 210, the ceramic composite coating can be heated and cooled in one or more cycles to remove entrained air bubbles in the ceramic composite coating.

Once the RF source 230 has been installed, the RF emitter 232 is conditioned to emit RF pulses at the frequency of the RF source. If the frequency of operation of the RF applicator 36 deviates from the frequency of the RF source 230, the RF applicator 36 is adjusted so that the frequency of operation of the RF applicator matches the frequency of the RF source 230. During adjustment of the RF applicator 36, the position of the RF emitter 232 within the recess 212 is changed either by increasing or decreasing the extent to which the RF source 230 extends into the recess. For example, decreasing the extent to which the RF source 230 extends into the recess 212 can be achieved by filing or grinding down the end of the RF emitter 232 or by placing one or more shims between the mounting flange 236 and the plinth 202. Increasing the extent to which the RF source 230 extends into the recess 212 can be achieved by adding one or more thin layers of conductive material to the end of the RF emitter 232 such as copper or aluminum tape or by removing one or more shims between the mounting flange 236 and the plinth, if they exist. Alternatively, dielectric material such as a thin disc of high permittivity, low loss material can be inserted into the recess 212 prior to installation of the RF source 230.

During thermoacoustic imaging, the RF emitter 232 of the RF source 230 is conditioned to generate short pulses of RF energy into the recess 212. The emitted RF energy pulses in turn travel along the insert 210 and then out of the RF applicator 36. Once the RF energy pulses travel out of the RF applicator 36, they are directed into the subject to deliver energy to tissue within the region of interest ROI of the subject S.

Thermoacoustic imaging can be used to contrast fat or fatty tissues with soft or lean tissues due to their lower electrical conductivity and permittivity in RF compared to other water and ion-rich soft or lean tissues. Fat and fatty tissues also have a lower absorption coefficient compared to soft or lean tissues like muscle. As such, during thermoacoustic imaging of a region of interest that includes a boundary between fat or fatty tissue and soft or lean tissue, bipolar acoustic signals are generated that are received by the thermoacoustic transducer 32. This is due to the fact that the soft or lean tissue absorbs more heat than the fat or fatty tissue causing it to expand rapidly across the boundary and into the fat or fatty tissue, that expands less, and then quickly contract. The strength or peak-to-peak values of the bipolar acoustic signals depend on the relative absorption properties of the fat or fatty tissue and the soft or lean tissue.

Different tissues have characteristic dielectric properties at particular frequencies. The dielectric properties determine how much energy is absorbed by tissue. When RF energy pulses are transmitted through tissue, the RF energy pulses are attenuated. The amount of attenuation can be determined using the dielectric properties of the tissue and the physical properties of the tissue. Fatty tissue absorbs less energy than lean tissue. As such, fatty tissue attenuates the RF energy pulses less than normal tissue. Using these properties, the amount of attenuation of tissue can be estimated and this may be used to determine how much fat is in the tissue.

Initially during imaging, a region of interest ROI within the subject S to be imaged that contains an object of interest and a reference separated by at least one boundary is located. In this embodiment, the region of interest ROI is located using the ultrasound imaging system 24. Specifically, ultrasound image data obtained by the ultrasound imaging system 24 is communicated to the computing device 22. The ultrasound image data is processed by the computing device 22 and a reconstructed ultrasound image is presented on the display device. The operator moves the ultrasound transducer 28 on the subject's body until the region of interest is located. When locating the region of interest, the computing device 22 overlays information associated with the angle of the centerline of the one or more transducer arrays 30 of the ultrasound transducer 28 overtop of the reconstructed ultrasound image on the display device. The information is used to provide feedback to the operator to ensure the axial axis of the ultrasound transducer 28 is generally perpendicular to a boundary between the object of interest and the reference.

At least one boundary between the object of interest and the reference is then identified in the reconstructed ultrasound image. In this embodiment, the at least one boundary is identified by the operator using an input device such as a mouse coupled to the computing device 22. Specifically, the operator draws a box that encompasses at least a portion of the object of interest, at least a portion of the reference and the identified boundary between the portions of the object of interest and the reference. The computing device 22 provides feedback to the operator via the display device to indicate the approximate angle between the box and the boundary to ensure the box is generally perpendicular to the boundary.

Since the angle α between the centerline of the one or more transducer arrays 30 of the ultrasound transducer 28 and the centerline of the one or more transducer arrays 34 of the thermoacoustic transducer 32 is known, the operator is able to adjust position of the thermoacoustic transducer 32 with respect to the subject's body such that the thermoacoustic imaging system 26 is able to obtain thermoacoustic image data of the region of interest at a desired imaging angle σ. The desired imaging angle σ is such that the centerline of the one or more transducer arrays 34 of the thermoacoustic transducer 32 extends through the boundary between the object of interest and the reference.

The thermoacoustic data are in turn communicated to the computing device 22 for processing. For example, the bipolar acoustic signals may be processed to estimate the fractional fat content of the object of interest, as described in U.S. Pat. Nos. 9,888,879, 9,888,880 and 9,980,677, the relevant portions of which are incorporated herein by reference.

Although the ceramic composite coating has been described above as being a high permittivity, ceramic wax composite, those of skill in the art will appreciate that the coating may be formed of other suitable material. For example, the coating may be in the form of a conductive paste or grease such as silver or graphite paste or grease that can readily fill air gaps between facing surfaces of the waveguide and the insert when the insert is positioned within the waveguide to fill its internal volume.

Alternatively, the coating may comprise ceramic powder and a gel wax. Potential gel wax compositions are described in U.S. Pat. Nos. 5,578,089 and 5,879,694.

In the examples described above, the coating is used to fill air gaps between a solid, high dielectric constant insert positioned within a waveguide of an RF applicator used for thermoacoustic imaging. Those of skill in the art will however appreciate that the coating may be used in other environments where an insert (solid or otherwise) is positioned within a waveguide and it is desired to fill air gaps between facing surfaces of the insert and the waveguide.

Although embodiments have been described above with reference to the accompanying drawings, those of skill in the art will appreciate that variations and modifications may be made without departing from the scope thereof as defined by the appended claims.

What is claimed is:

1. A radio frequency applicator comprising:
   an open-ended, hollow waveguide having an aperture therein;
   a solid dielectric insert within the waveguide, the solid dielectric insert having a recess formed therein that is aligned with said aperture;
   a filler material between facing surfaces of the waveguide and the solid dielectric insert to fill gaps therebetween, wherein the filler material has a dielectric constant that is similar to that of the solid dielectric insert; and
   a radio frequency (RF) source extending through the aperture and into the recess and being configured to generate RF energy pulses.

2. The radio frequency applicator of claim 1 wherein the solid dielectric insert is formed of ceramic material.

3. The radio frequency applicator of claim 2 wherein the solid dielectric insert has a real relative permittivity greater than 10 and a loss tangent less than 0.01.

4. The radio frequency applicator of claim 3 wherein the solid dielectric insert has a real relative permittivity between about 57 and 63.

5. The radio frequency applicator of claim 1 wherein the filler material has a melting point in the range of from about 40 and 120 degrees Centigrade.

6. The radio frequency applicator of claim 5 wherein the filler material is a ceramic wax composite.

7. The radio frequency applicator of claim 5 wherein the filler material is a ceramic wax composite having a real relative permittivity between about 30 and 50 and an imaginary relative permittivity between about 2 and 7 and the insert is formed on ceramic material having a real relative permittivity between about 57 and 63.

8. The radio frequency applicator of claim 1 wherein the filler material has a real relative permittivity between about 30 and 50 and an imaginary relative permittivity between about 2 and 7.

9. The radio frequency applicator of claim 8 wherein the filler material is a ceramic wax composite.

10. The radio frequency applicator of claim 9 wherein the ceramic wax composite has a melting point in the range from 40 and 120 degrees Centigrade.

11. The radio frequency applicator of claim 10 wherein the ceramic wax composite comprises 69% to 80% by weight titanium dioxide, 10% to 15% by weight wax and 4% to 13% by weight graphite.

12. The radio frequency applicator of claim 1 wherein the filler material is one of: (i) a ceramic wax composite; (ii) a conductive paste; (iii) a conductive grease; and (iv) a ceramic powder and gel wax mixture.

* * * * *